US009058636B2

(12) United States Patent
Schwarz et al.

(10) Patent No.: US 9,058,636 B2
(45) Date of Patent: Jun. 16, 2015

(54) SYSTEM AND METHOD FOR PATHOLOGY SPECIMEN COLLECTION

(71) Applicants: Brian K. Schwarz, Lake in the Hills, IL (US); Raymond J. Bender, Elgin, IL (US); Patrick J. Heniff, Yorkville, IL (US)

(72) Inventors: Brian K. Schwarz, Lake in the Hills, IL (US); Raymond J. Bender, Elgin, IL (US); Patrick J. Heniff, Yorkville, IL (US)

(73) Assignee: Lattice Incorporated, Wheaton, IL (US)

( * ) Notice: Subject to any disclaimer, the term of this patent is extended or adjusted under 35 U.S.C. 154(b) by 81 days.

(21) Appl. No.: 13/740,722

(22) Filed: Jan. 14, 2013

(65) Prior Publication Data
US 2014/0117080 A1 May 1, 2014

Related U.S. Application Data

(60) Provisional application No. 61/720,030, filed on Oct. 30, 2012.

(51) Int. Cl.
*G06F 17/00* (2006.01)
*G06Q 50/22* (2012.01)
*G06F 19/00* (2011.01)
*G06Q 10/08* (2012.01)

(52) U.S. Cl.
CPC .............. *G06Q 50/22* (2013.01); *G06F 19/366* (2013.01); *G06Q 10/087* (2013.01)

(58) Field of Classification Search
USPC ................ 235/375, 380, 462.07–12
See application file for complete search history.

(56) References Cited

U.S. PATENT DOCUMENTS

| 2004/0005245 | A1* | 1/2004 | Watson et al. | 422/65 |
| 2010/0004779 | A1* | 1/2010 | Markin | 700/227 |
| 2010/0036676 | A1* | 2/2010 | Safdi et al. | 705/2 |
| 2010/0315205 | A1* | 12/2010 | Egbert | 340/10.51 |

OTHER PUBLICATIONS

Web page for product information of "NovoPath Software Advancing Patient Diagnostics," at http://www.novopath.com/pages/solutions/novobath/default.aspx, accessed Jun. 14, 2013.
Brochure—"NovoPath Anatomic Pathology Software Platform." 6 pages, accessed Jun. 14, 2013.

* cited by examiner

Primary Examiner — Daniel St Cyr
(74) Attorney, Agent, or Firm — Erin J. Fox; Barnes & Thornburg LLP (57) ABSTRACT

A computer-implemented method for labeling and tracking a pathology specimen after collection and positive patient identification comprises the step of creating a pathology specimen record with a unique specimen identification code for at least one specimen. The method further includes the step of creating a label for application to a container holding the specimen, wherein the label includes the unique specimen identification code and creating an order with a unique accession number after the container is forwarded for processing, by scanning the label. The unique identification code is utilized for tracking purposes to ensure that pathology specimens for the positively identified patient are not lost in transit to the pathology laboratory for further processing. This improves quality to the patient by the elimination of transcription errors, identification of missing or lost specimens, and confirmation that pathology specimens are correctly matched to a patient.

16 Claims, 12 Drawing Sheets

PRIOR ART
FIG. 1

Please identify the patient by
scanning the correct field data.

ALLEN, ANGELO JOHN IV

DOB: 1962-06-29     Sex: M
Age: 50             Bed: W440A

FIN: 1765432

☐ Patient identity confirmed

<ID not checked reason>

[Unavailable]  [Cancel]

PRIOR ART

FIG. 2

PRIOR ART

FIG. 3

PRIOR ART

FIG. 4

PRIOR ART

| Pathology Order Receive | |
|---|---|
| Lattice ID: | D3-1837 |
| Requisition #: | << |
| Patient FIN: | 8823456 |
| Patient Name: | GARCIA, ROSALYN A |
| Surgery Room: | SURG1 |
| Surgeon: | 01234    Welby, Marcus A. MD |
| Nurse: | Nurse    Nurse, Nurse |
| Date/Time: | SU   11/02/2003   1200   R |
| Procedure: | Gall Bladder |
| Comments: | |
| Pre-OP Diag: | Gallstones |
| Post-OP Diag: | Same |

| Lattice ID | Tissue Code | Specimen Description |
|---|---|---|
| D3-1837-2 | 110 | Fundus |
| D3-1837-1 | 110 | Neck |

Next Specimen: [    ]   Add        Barcodes

Receive    Cancel

SYSTEM AND METHOD FOR PATHOLOGY SPECIMEN COLLECTION

CROSS-REFERENCE

This application claims the benefit of U.S. Provisional Patent Application No. 61/720,030, filed on Oct. 30, 2012, and entitled "Specimen Collection for Pathology," the entire disclosure of which is incorporated herein.

BACKGROUND

1. Field of the Disclosure

The present disclosure relates to systems and methods for collecting specimens and, more particularly, to systems and methods for collecting pathology specimens.

2. Description of the Background

During a doctor visit or a hospital stay, patients are oftentimes required to leave a sample of urine, blood, stool, or other biological sample for analysis. In addition, in outpatient or inpatient scenarios, doctors, nurses, or other healthcare professionals may collect tissue, fluid, a foreign body, a tumor, or other pathology specimen for analysis. Whether a biological or a pathology specimen is collected, specific procedures must be followed to prevent contamination and to properly track the specimen as belonging to a particular patient. These procedures may be very different for biological and pathology specimens.

Figure 1:
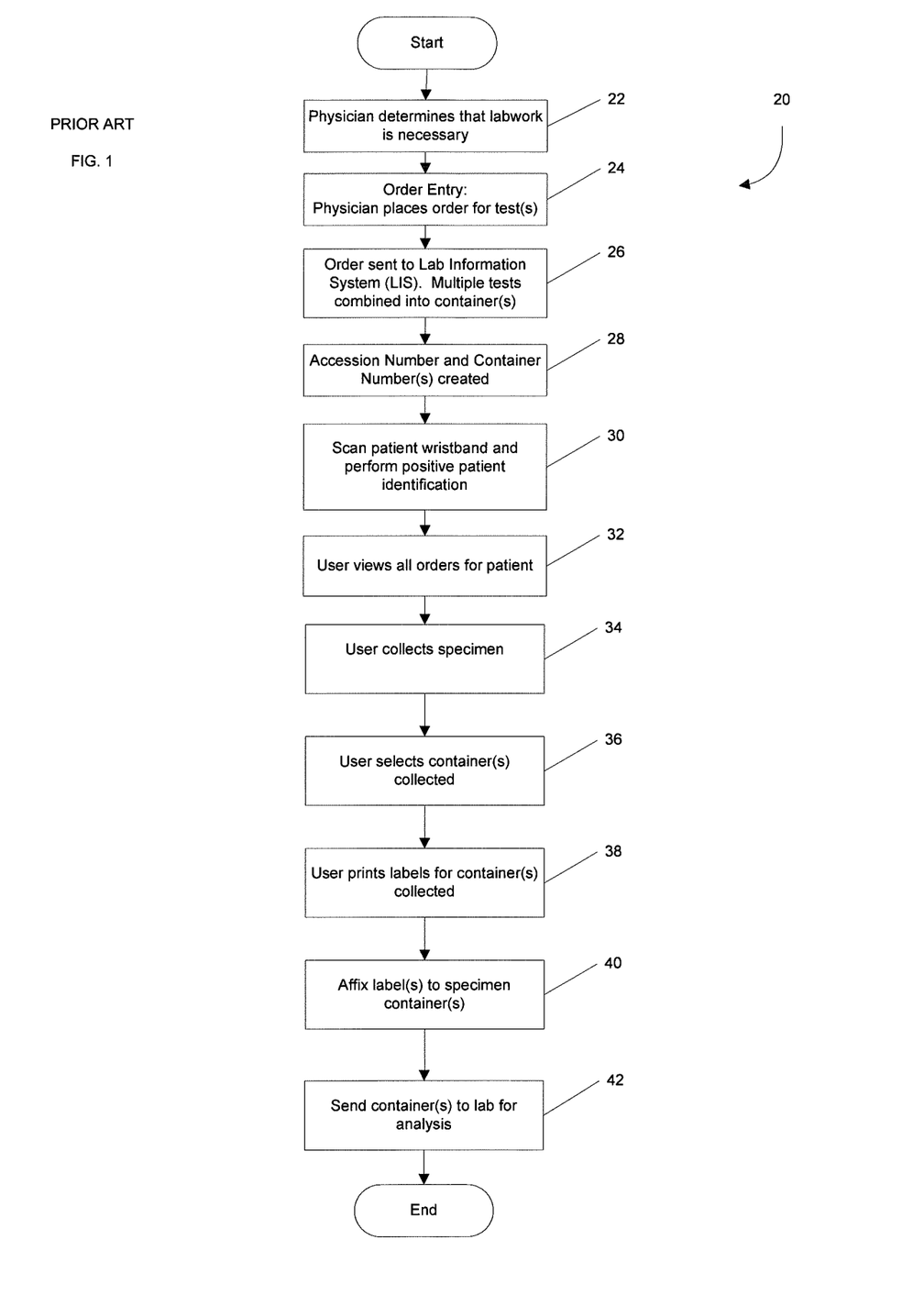
FIG. 1 is flow diagram depicting method steps taken during operation of a prior art system for collection of a biological specimen.
Figure 2:
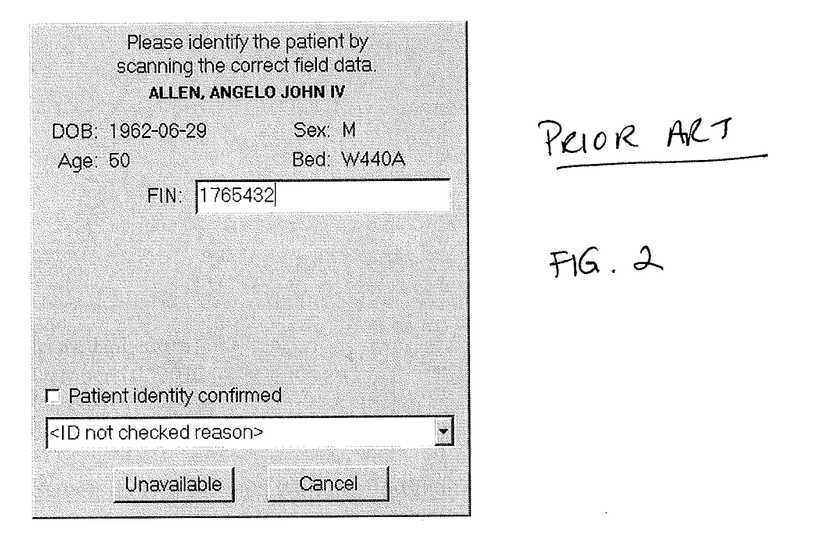
FIGS. 2-4 are screen shots displayed during operation of the prior art system of FIG. 1.

A prior art method 20 for collection of biological specimens, such as blood, urine, stool, or other biological samples, is depicted in FIG. 1. During a medical evaluation, a physician or other healthcare professional determines at block 22 that labwork is necessary. The physician then places an order for one or more tests at block 24 and thereafter sends the order to a Laboratory Information System (LIS) at block 26, which is a system that receives, processes, and stores information generated by medical laboratory processes. An accession number is created for the order and one or more container number(s) are created for the order and the specimens, respectively, at block 28.

Figure 3:
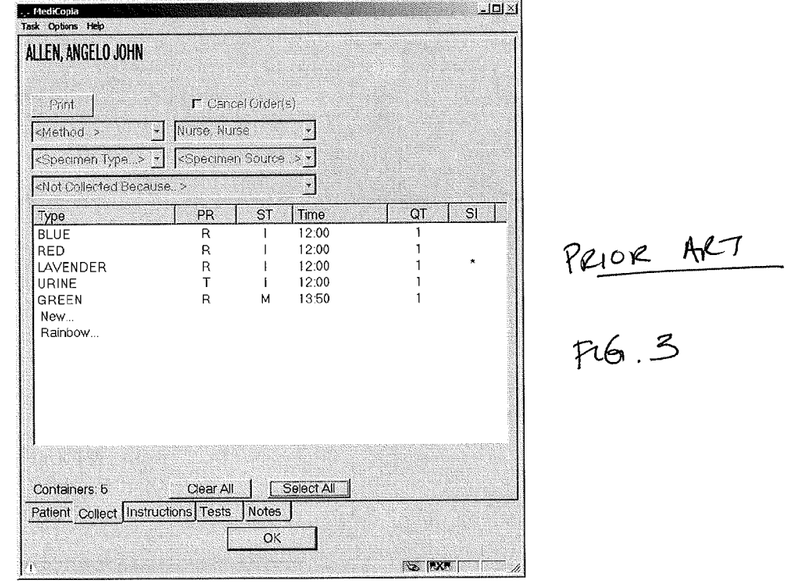

Still referring to FIG. 1, at block 30, a wristband that is attached to a wrist of the patient is scanned to perform a positive patient identification. Once the wristband is scanned, patient information will be displayed on a screen on a monitor or other visual display. The patient information may include the patient's name, date of birth, sex, bed number, age, patient number, or any other relevant patient information. The user of the system 20, which is likely a healthcare professional, thereafter confirms the patient's identification. The system proceeds to the screen seen in FIG. 3 at block 32, wherein the screen displays all orders for the patient.

Figure 4:
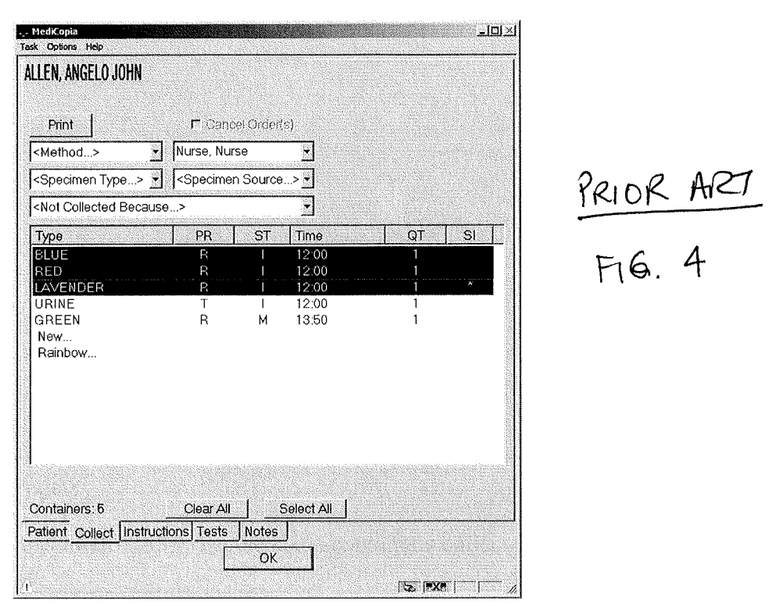

The healthcare professional proceeds with collection of the specimen at block 34 and selects one or more containers for collection at block 36. Specifically, the healthcare professional selects all containers that have been collected from the screen shown in FIG. 4. The healthcare professional then prints one or more labels for the container(s) at block 38 and affixes the labels to the appropriate container(s) at block 40. The one or more containers are thereafter forwarded to one or more laboratories for analysis at block 42.

As noted above, procedures for biological specimen collection differ from procedures for pathology specimen collection. The current electronic processes for biological specimen collection are not practical for pathology specimen collection. With biological specimen collections, necessary laboratory tests are generally identified ahead of time based on procedure, symptoms, etc. For example, a patient complaining of chest pain may automatically receive a cardiac profile or a patient with a history of cancer may automatically have a liver panel done. In biological specimen collection, a healthcare professional may therefore use their system to place an order for laboratory tests and the LIS may create an accession number before the sample is collected. This accession number is a unique identification that is used throughout the analysis process. In contrast, physicians and surgeons generally do not know ahead of time whether a pathology specimen will need to be collected (i.e., the physician or surgeon may not know until they are in the middle of a procedure what testing will be required). Pathology specimens therefore do not have a pre-collection accession number. Existing specimen collection applications therefore do not have the capability of creating uniquely-identified pathology labels for tracking of pathology specimens.

Figure 5:
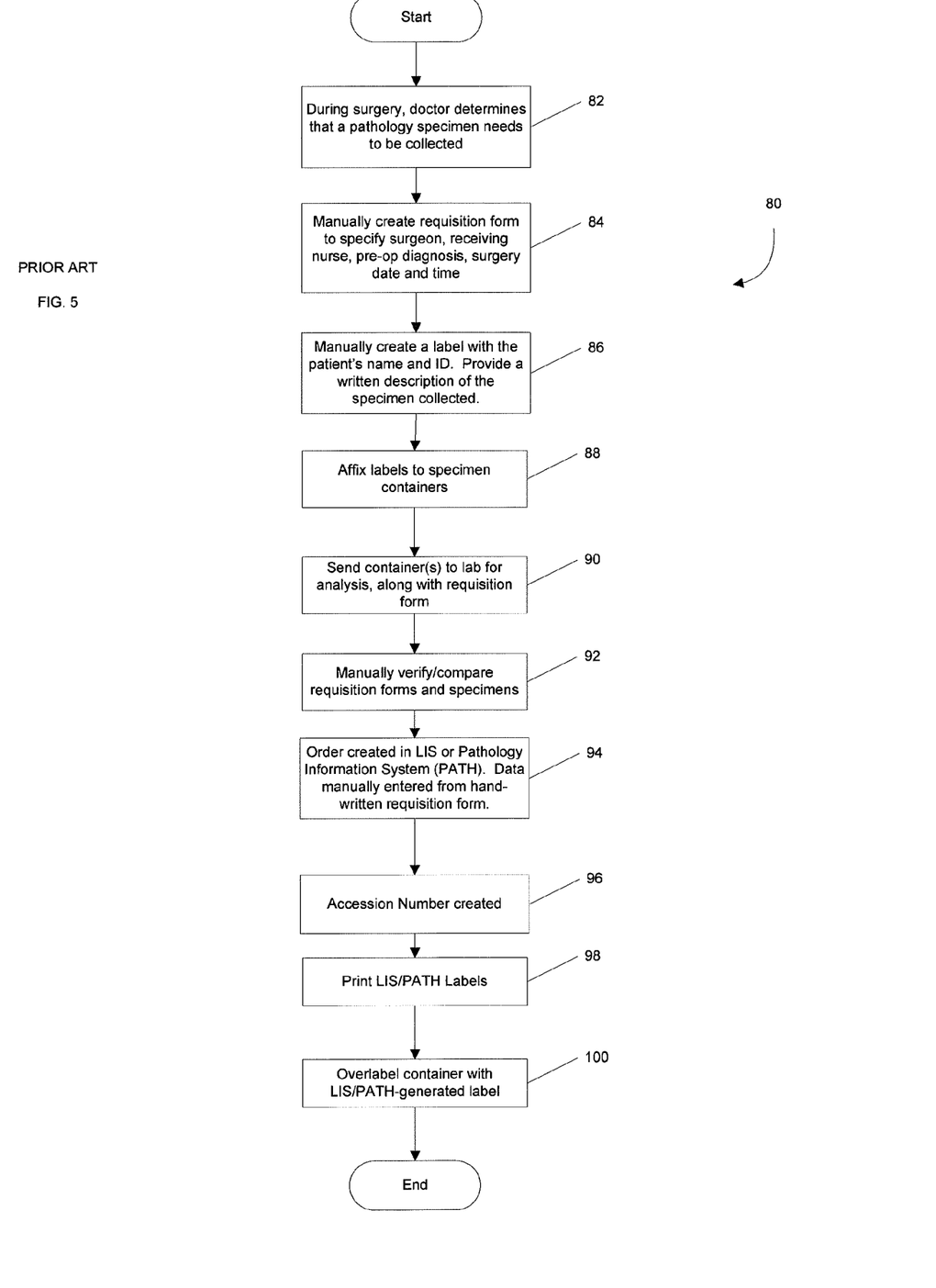
FIG. 5 is a flow diagram depicting steps taking during a manual collection of a pathology specimen.

A prior art manual system and method 60 for collection of pathology specimens, such as tissue, fluid, a foreign body, a tumor, or any other pathology specimen, is depicted in FIG. 5. Prior to a surgical procedure, a patient is identified by a nurse, physician, or other healthcare professional, generally by asking the patient their name, date of birth and possibly checking their medical record number (MRN), financial identification number (FIN), and/or visit number manually. The MRN is an identification number given to a patient by a particular hospital. The FIN is an identification number that is assigned to a patient for a particular visit or patient encounter and is used for billing purposes. During a surgical procedure, a doctor may determine that a pathology specimen needs to be collected (at block 82). A requisition form or similar request documentation or mechanism is manually created prior to or during the surgical procedure at block 84 to specify information, such as the surgeon, the receiving nurse, a pre-operative diagnosis, and the surgery date and time. At block 86, one or more labels is thereafter manually created with the patient's name and identification, for example, the patient's MRN or FIN, and a written description of the specimen collected. The label(s) is affixed to one or more specimen containers at block 88 and the container(s) are forwarded to the laboratory for analysis at block 90, along with the requisition form.

At the laboratory, staff manually compares and verifies the requisition forms or similar request documentation or mechanism and the pathology specimens at block 92 and creates an order in a computer system, such as a Laboratory Information System (LIS) or Pathology Information System (PATH) system, at block 94. Data is manually entered into the computer system from the written requisition form. An accession number is created at block 96 and labels are printed at block 98 from a LIS/PATH system, which is a system that integrates operations of testing laboratories. The container is thereafter overlabeled by placing the LIS/PATH label(s) over the manually-generated label(s) from block 86 at 100.

The current manual process for pathology specimen collection is very time consuming and error prone. This results from a number of factors, including the lack of positive patient identification using a computer-based system, lack of a unique identification number for each collected specimen, lack of tracking using a unique specimen identifier from point of collection to the remote laboratory for processing, and the manual input of patient and anatomical descriptions about the pathology specimen available only at the time of collection (not at the time of data entry in the remote pathology lab).

SUMMARY

In an illustrative embodiment, a computer-implemented method for tracking and processing a pathology specimen after collection comprises the step of creating a pathology specimen record with a unique specimen identification code for at least one specimen. The method further includes the step of creating a label for application to a container holding the specimen, wherein the label includes the unique specimen identification code and creating an order with a unique accession number after the container is forwarded for processing, by scanning the label.

In a further illustrative embodiment, a computer-implemented method for tracking and processing a pathology specimen after collection comprises the step of creating a requisition with a unique requisition identification, wherein the requisition is based on at least one specimen. The method further includes the step of creating a pathology specimen record with a unique specimen identification code for the at least one specimen. Still further, the method includes the steps of creating a first label including the unique requisition identification for association with a requisition form and creating a second label including the unique specimen identification code for association with the at least one specimen. The method still further includes the step of creating an order with a unique accession number after the requisition form with first label and the at least one specimen with second label are forwarded for processing, by scanning the first or second label.

In another illustrative embodiment, a computer system for tracking and processing a pathology specimen comprises at least one processor, a network interface, and a memory element coupled to the processor. The memory stores instructions to direct the processor to perform operations comprising creating a pathology specimen record with a unique specimen identification code for the at least one specimen. The operations further include creating a label for application to a container holding the specimen, wherein the first label includes the unique specimen identification code and creating an order with a unique accession number after the container has been forwarded for processing, by scanning the label.

BRIEF DESCRIPTION OF THE DRAWINGS

Other aspects and advantages of the present disclosure will become apparent upon consideration of the following detailed description, wherein similar structures have like or similar reference numerals.

DETAILED DESCRIPTION

The present disclosure is directed to systems and methods for pathology specimen collection. While the systems and methods of the present disclosure may be embodied in many different forms, several specific embodiments are discussed herein with the understanding that the present disclosure is to be considered only as an exemplification of the principles of the disclosure, and it is not intended to limit the disclosure to the embodiments illustrated.

Figure 6:
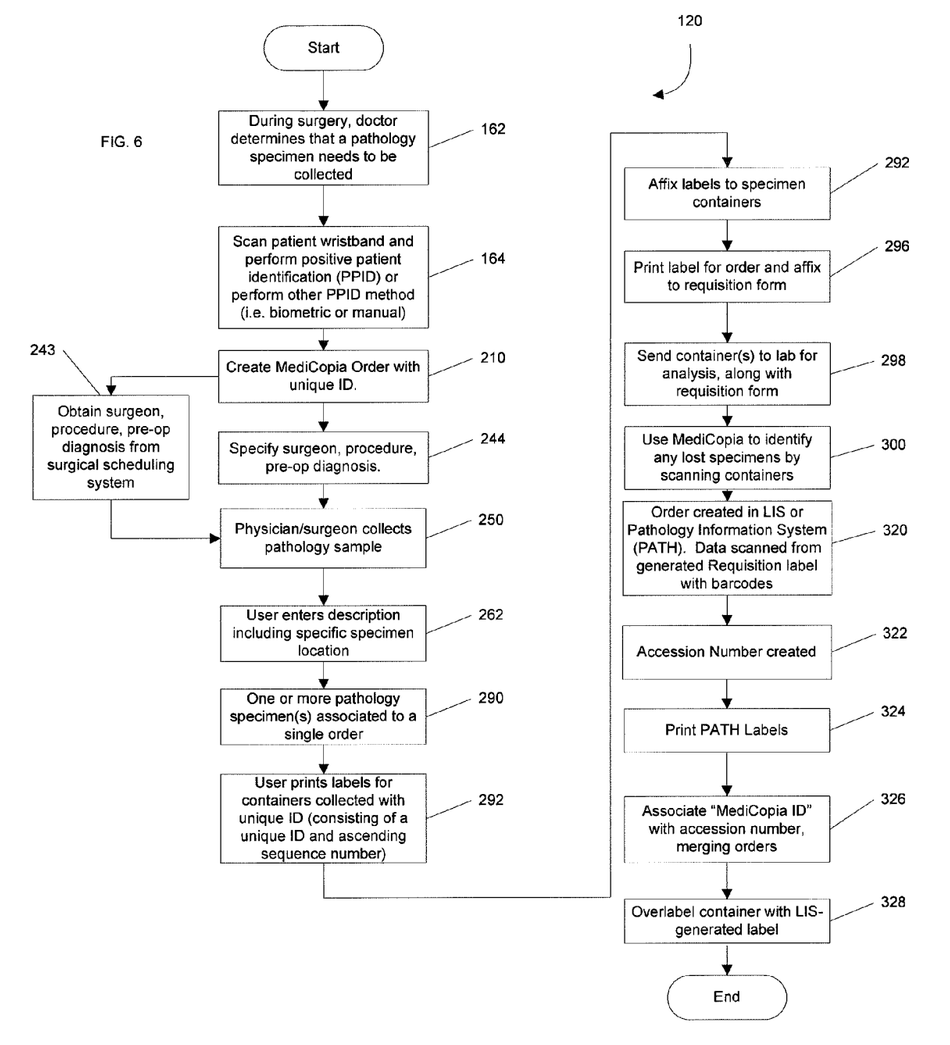
FIG. 6 is a flow diagram depicting method steps taken during operation of a system for collection of a pathology specimen of the present disclosure.
Figure 7:
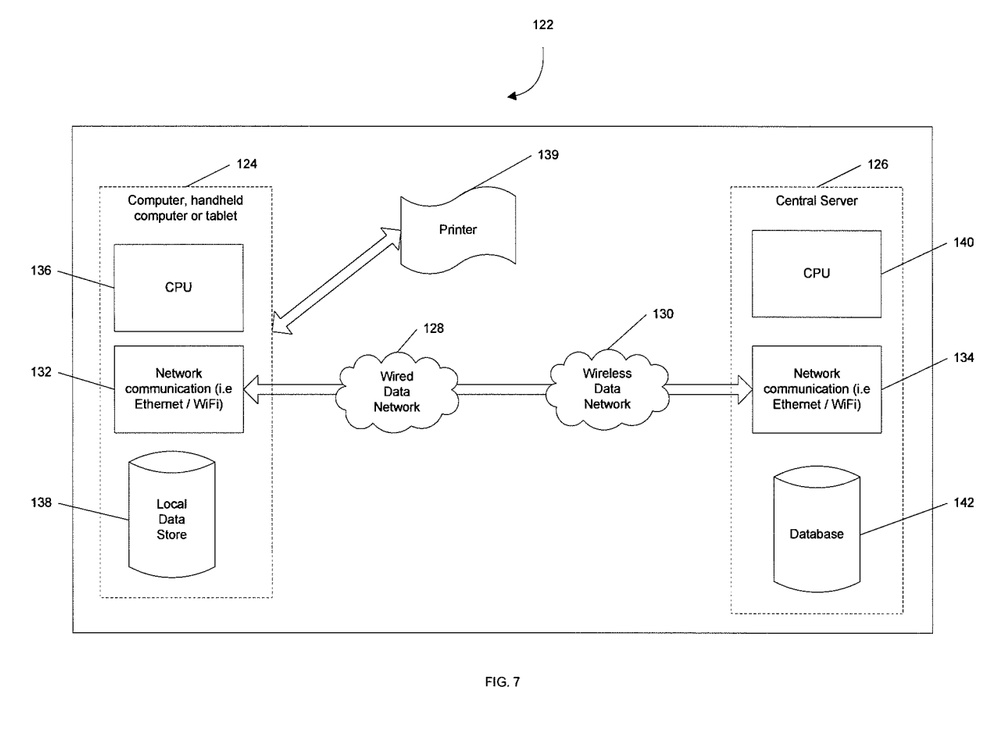
FIG. 7 is a schematic diagram of a system for implementing the method steps of FIG. 6 for collection of a pathology specimen.

Referring to FIG. 6, a method for pathology specimen collection 120 is depicted in the form of a flow diagram. The method is at least partially implemented by a networked system 122, as seen in FIG. 7, which enables communication between one or more electronic platforms 124, for example, computers, handheld computers, tablets, and/or other electronic platforms and one or more central server 126. The system 122 may include any number of electronic platforms 124 connected through a wired data network 128 and/or a wireless data network 130 to each other and/or the central server 126. The wired data network 128 may be a global network, a wide area network, or a local area network. The wireless data network 130, which may be coupled to the wired data network 128, may include one or more wireless data networks, such as cellular networks, WiFi networks, Bluetooth networks, etc. The electronic platforms 124 and/or the central server 126 may be coupled to both the wired data network 128 and the wireless data network 130 through a network communication device 132 within the electronic platform 124 and a network communication device 134 within the central server 126. In an illustrative embodiment, the electronic platforms 124 may couple to the wired data network 128 over wired connections and to the wireless data network 130 over wireless links. In this manner, the electronic platforms 124 may access the central server 126 through the wired data network 128 and/or the wireless data network 130.

Referring again to FIG. 7, each electronic platform 124, which may be, for example, a computer, a handheld computer, a tablet, or any other suitable electronic platform, may include a graphical user interface (not shown) and a computer portion. The graphical user interface may include one or more input/output (I/O) devices, such as a touch screen, a keyboard, a stylus, a joystick, or any other suitable I/O device, which can be arranged in various manners and have different shapes or designs. The touch screen may be a liquid crystal display (LCD), a display screen, a plasma screen, a light emitting diode (LED), or any other screen capable of displaying text and/or images and/or allowing input of text. The computer portion may also include an I/O device, a central processing unit (CPU) 136 (i.e., a microprocessor), memory (not shown), and a local data store or database 138. The CPU 136 may be any computer-processing unit, including multi-processor or single processor configurations. The memory may include, without limitation, any one or a combination of volatile memory elements (e.g., random access memory (RAM, such as DRAM, SRAM, SDRAM, etc.)) and nonvolatile memory elements (e.g., ROM, hard drive, tape, CDROM, etc.). The memory may incorporate electronic, magnetic, optical, and/or other types of storage media, and may have a distributed architecture where various components are situated remote form one another, but may still be accessed by the CPU 136, such as cloud computing. The graphical user interface is coupled to the I/O device such that commands or data entered by a user through the graphical user interface will be forwarded to the I/O device, to the CPU 136, and then to the memory.

The method for pathology specimen collection 120 as disclosed herein may be in the form of one or more executable programs stored within the memory that are run within the CPU 136 (or other hardware device) or may be accessed through an Internet website accessible from any location. If an Internet website is utilized, the Internet website may include any number of different security features. The one or more executable programs, if run within the CPU 136, may be implemented in software, firmware, hardware, or a combination thereof. The local data store 138 may store data related to specimens and/or any other data.

The method 120 may be embodied in any computer-readable medium for use by or in connection with an instruction execution system, apparatus, or device, such as a computer-based system, processor-containing system, or other system that may fetch the instructions from the instruction execution system, apparatus, or device and execute the instructions. In the context of this application, a "computer-readable medium" may be any means that may store, communicate, propogate, or transport the program for use by or in connection with the instruction execution system, apparatus, or device. The computer readable medium may be, for example, but not limited to, an electronic, magnetic, optical, electromagnetic, infrared, or semiconductor system, apparatus, device, or propagation medium. More specific examples (a non-exhaustive list) of the computer-readable medium would include the following: an electrical connection (electronic) having one or more wires, a portable computer diskette (magnetic), a random access memory (RAM) (electronic), a read-only memory (ROM) (electronic), an erasable programmable read-only memory (EPROM, EEPROM, or Flash memory) (electronic), an optical fiber (optical), a portable compact disc read-only memory (CDROM) (optical), and a portable USB storage device. In an illustrative embodiment, where the method 120 is implemented in hardware, it should be obvious that it may also be implemented with any, or a combination of, the following technologies, which are each well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

One or more electronic platforms 124 may be connected, either wirelessly or through a wired connection, to a printer 139. Optionally or additionally, one or more of the electronic platforms 124 may be connected to any other suitable peripheral devices, for example, a camera, a video camera, scanner, plotter, microphone, or any other suitable peripheral device.

Referring again to FIG. 7, the central server 126 further includes a CPU 140 and a central database 142. The electronic platform(s) 124 communicates via the wired data network 128 and/or the wireless data network 130 with the central server 126 through the network connections 132, 134, to transfer data to the central server 126 for processing within the CPU 140 and/or storage within the database 142. Data may also be transferred from the central server 126 to the electronic platform(s) 124 for displaying and/or processing by the electronic platform(s) 124.

While various components of the system 122 are disclosed, the system 122 may include any number of the depicted or additional electronic components, such as central processing units, monitors, printers, other peripheral device, and/or any other computer hardware or software.

Figure 8:
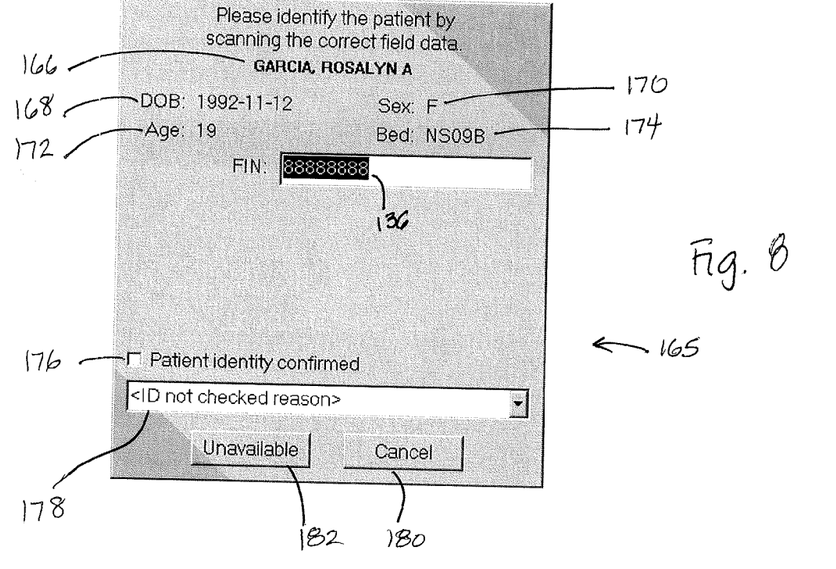
FIGS. 8-12 are screen shots displayed during operation of the system of FIG. 6.

Prior to surgery, a medical professional or assistant in the operating room or other facility logs into the system by way of an electronic platform 124 within the facility. The method 120 runs on the electronic platform 124 by way of software installed on the electronic platform or through the electronic platform 124 accessing the software installed on the central server 126 or other remote device, as described above. During a surgical procedure, a doctor may determine that a pathology specimen is necessary at block 162. For example, a physician may encounter a mass, tumor, or other specimen that may need to be collected, biopsied, and/or analyzed. A wristband attached to the patient's wrist is scanned at block 164 of FIG. 6 (or other positive patient identification method, such as manual verification or biometric identification) to perform positive patient identification (PPID). At this step of the process, the screen 165 of FIG. 8 is displayed on a monitor, television, or other visual display. The screen 165 will include patient information including, for example, a patient name 166, a patient date of birth 168, a patient sex 170, a patient age 172, a patient bed 174 (if inpatient), and a patient identification code 176. The screen 165 may also include a check box 176 for indicating that an identity of the patient has been checked and/or a drop down box 178 for indicating a reason why an identity of the patient was not checked. A user of the system may select a "Cancel" button 180 to exit the screen 165 or an "Unavailable" button 182 to proceed with a requisition or order in case the patient is not available. This allows a medical professional or caregiver to review patient and/or pathology history information, without needing to have a patient wristband or similar positive-patient identification. The "Unavailable" button 182 is used only to review information, not to print labels at collection time, which requires positive patient identification. If the "Unavailable" button 182 is depressed, the system proceeds to a screen 190.

Figure 9:
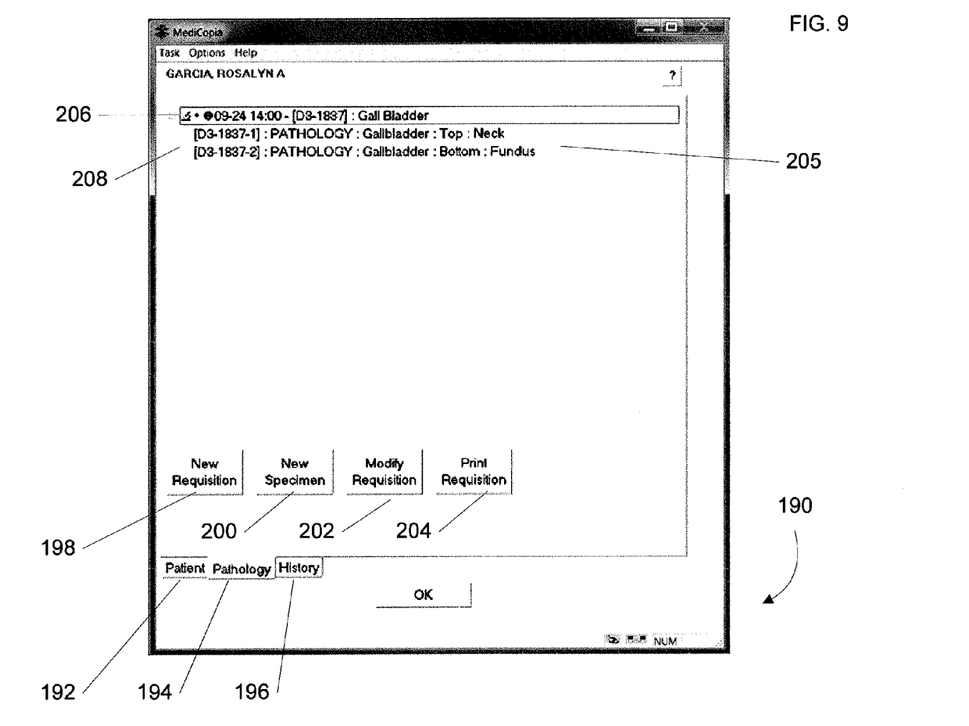

Once the identity of the patient has been confirmed at screen 165, the screen 190 appears with the patient's name and any entered requisitions or specimens. The screen 190 includes three tabs, a first for patient demographic information 192, a second for pathology information 194, and a third for patient history 196 including prior requisition forms and collected specimens. On the pathology information tab 194, a new requisition may be created by depressing the "New Requisition" button 198 or a new specimen for a requisition may be created by depressing the "New Specimen" button 200. A requisition is a new request for pathology processing submitted by a doctor or other medical professional. A requisition has a unique requisition identification and may include one or more specimens each having a unique specimen identification. The requisition and specimen identifications may be number-based or may be any code that includes one or more of letters, numbers, alpha-numeric characters, or any other characters. A requisition may be modified by depressing the "Modify Requisition" button 202 and the requisition may be printed by depressing the "Print Requisition" button 204. Each requisition will be shown in a tree 205 as a main node 206 and each specimen will be shown in the tree 205 as a sub-node 208 of the main node 206 to which it belongs. Any number of main nodes 206 representing requisitions and any number of sub-nodes 208 representing specimens may be depicted in the tree 205.

Figure 10:
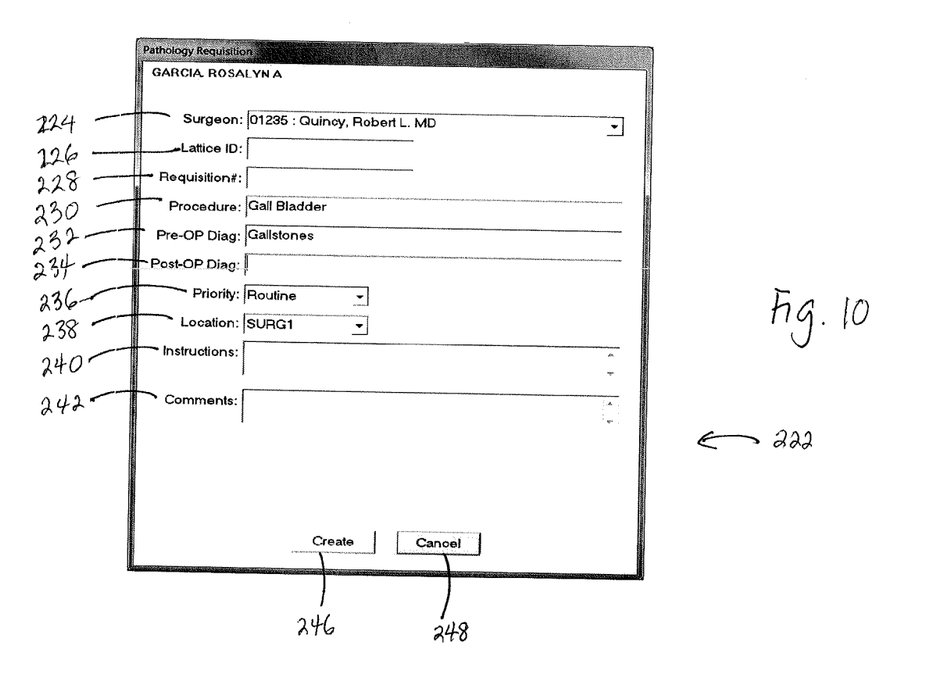

When the "New Requisition" button 208 on the screen 200 is depressed, at block 210 of FIG. 6, the system proceeds to a screen 222, as seen in FIG. 10. The screen 222 allows for creation of an order with a unique order identification code or number in an LIS/PATH system (or other similar or suitable system). Specifically, the screen 222 includes fields for a surgeon name 224, a unique order identification code for the overall order 226, a requisition identification code 228, a type of procedure 230, a pre-operative diagnosis 232, a post-operative diagnosis 234, a priority level 236, a location 238, any instructions 240, and any comments 202. Some or all of the information on screen 222 (FIG. 10) may be obtained through an interface to a surgical scheduling software application at block 243. Optionally, information may be inserted at a block 244 into the fields on the screen 222. In either situation, when the correct information has been populated, the user may depress a "Create" button 246 to create the requisition order with unique order identification code. Optionally, at screen 222, a user may depress a "Cancel" button 248 to exit the screen 192 or the method 120.

Figure 11:
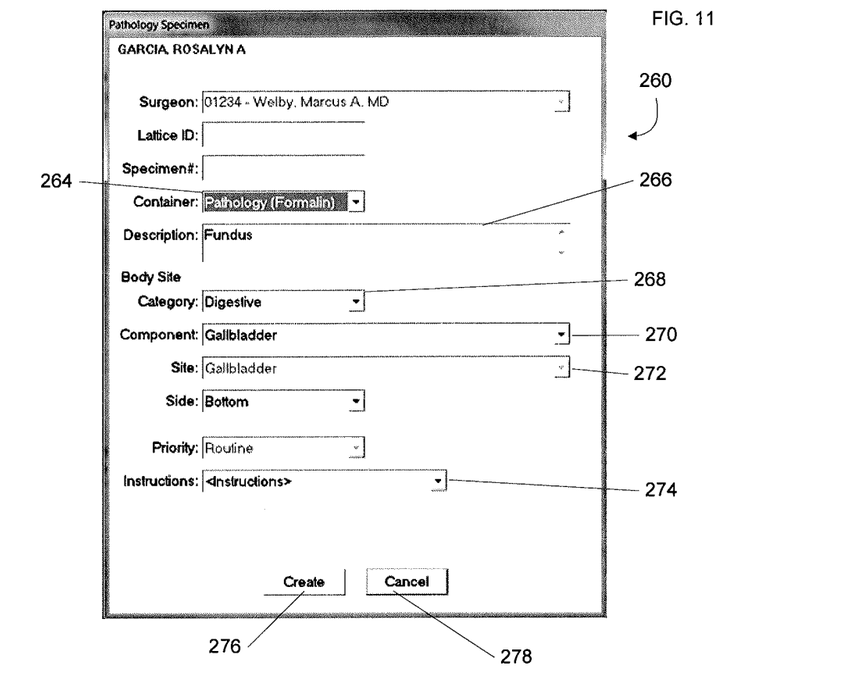

After information has been inserted into the screen 222 and the requisition has been created, the physician, surgeon, or other medical professional collects one or more pathology samples at block 250. For each pathology specimen created, a pathology specimen record is created using a screen 260. In particular, at block 262 of FIG. 6, information is inserted into the screen 260. For example, the screen 260 may include a container drop down menu 264, a box for insertion of a description of the specimen 266, a body site category drop down menu 268, a component body site drop down menu 270, a side drop down menu 272, and an instructions drop down menu 274. One or more of the fields in the screen 262 may be automatically populated from information provided in one or more previous screens or dependent on information inserted into the screen 222. One or more of the fields in the screen 262 may additionally or alternatively be grayed out such that a user may not change such fields. Once all necessary fields are completed, a user may depress a "Create" button 276 to create a specimen record. The user is presented with a print dialog and typically prints a specimen label and immediately affixes it to the specimen. Optionally, a user may depress a "Cancel" button 278 to exit the screen 260 or the process.

At block 290 of FIG. 6, additional specimen records may be created for each individual specimen to be collected. A label is created and applied to each container associated with each specimen, wherein each label includes the unique specimen identification code for that specimen. Each unique specimen identification code includes the requisition identification code and a unique ascending sequence code. The user then prints a label for the requisition, which includes the unique requisition identification code. The user thereafter affixes the label to the requisition form at block 296. In alternative illustrative embodiments, the requisition form may be eliminated and/or the requisition form may be hand-written, in which case, labels may not be affixed to the requisition form.

Figure 12:
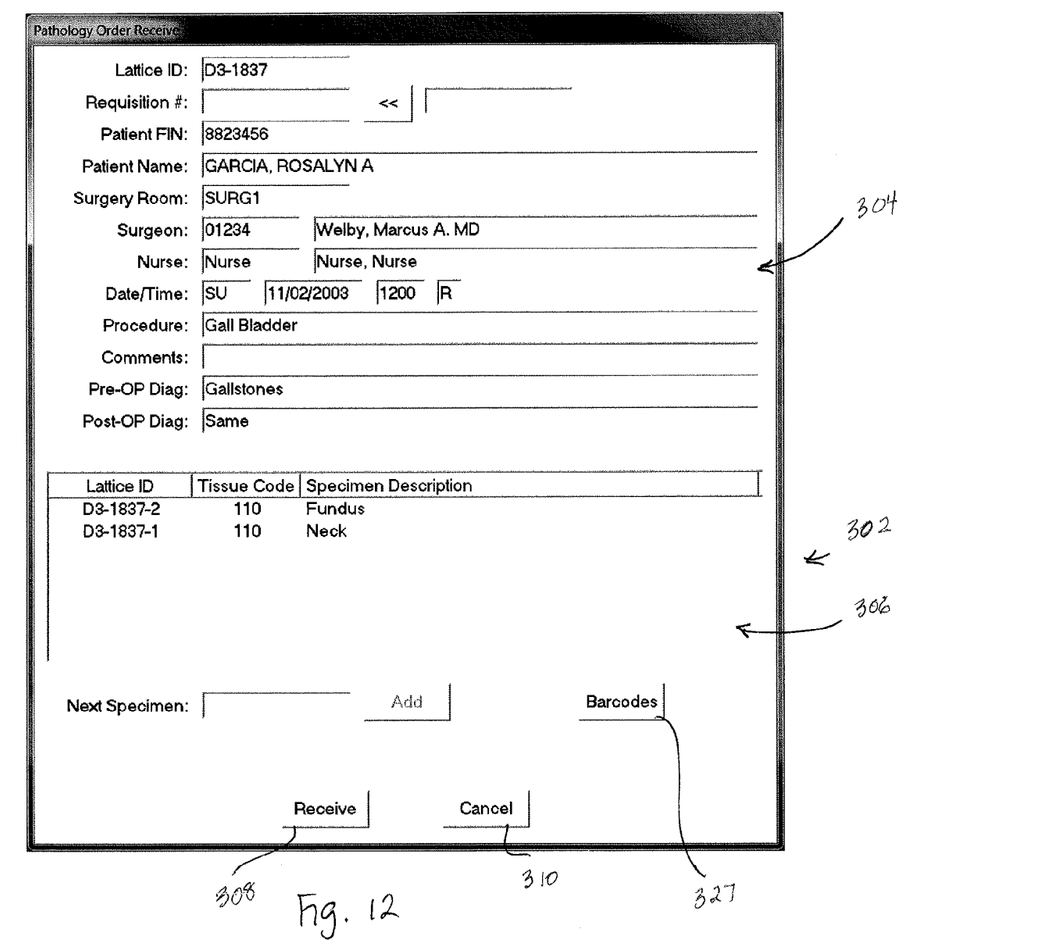
Figure 13:
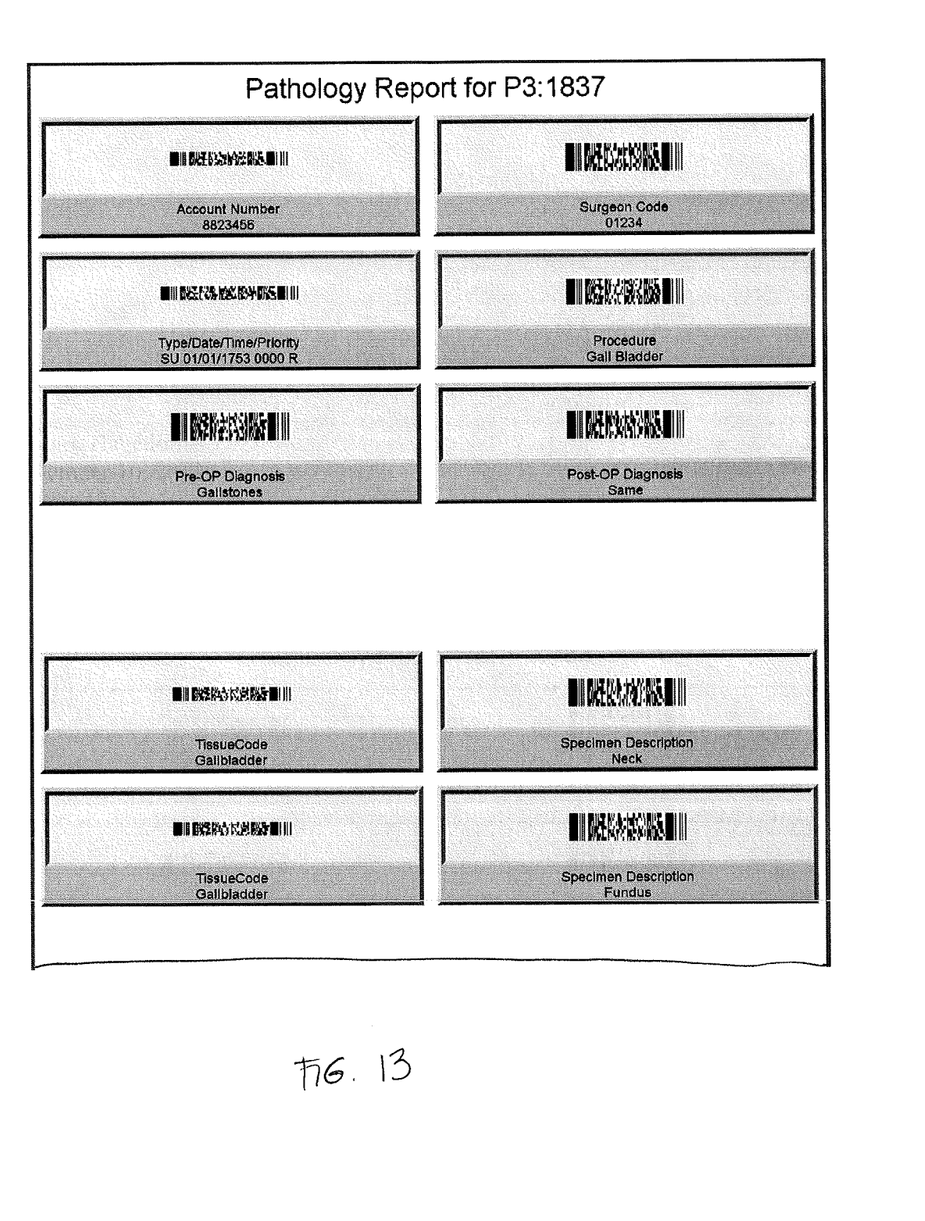
FIG. 13 depicts sample barcodes for entering of information into, for example, an LIS/PATH system.

Once the appropriate labels are affixed to the specimen container(s) and/or the requisition form, the container(s) and requisition form are forwarded to the laboratory for analysis at block 298. Once received at the laboratory, the requisition form and/or the container(s) are scanned at block 300. During this process, the screen 304 of FIG. 12 appears on a monitor, television, tablet, or other visual display at the laboratory. An upper portion 304 of the screen may include patient information and information related to the collection of the pathology specimen(s) (e.g., surgeon, nurse, data, time, procedure, etc.). A lower portion 306 of the screen may include a listing of each of the pathology specimens that should have been received by the laboratory. Each pathology specimen may be identified by its unique specimen identification code, a tissue code, and a specimen description. Optionally, additional and/or different specimen information may be included. A histologist or other medical professional scans all of the associated specimens for the requisition in the correct sequence. As each specimen is scanned, the specimen is added to the list of specimens displayed on the screen 304. When the last specimen is scanned, a "Receive" button 308 is enabled and may be depressed. Optionally, the user may depress a "Cancel" button 310 to exit the screen 302 or the process.

At block 320 of FIG. 6, an order is created in the LIS/PATH system by scanning barcodes on the labels that were placed on the requisition form in block 256. Alternatively, the order may be created by scanning the barcodes on the labels that were placed on the specimen containers and/or both the specimen containers and the requisition form. Regardless of what labels are scanned, an accession number is automatically created at block 322 and LIS/PATH labels are printed at block 324. At block 326, a MediCopia or system identification is associated with the accession number to merge the orders together. In the system 122 that implements the method of FIG. 6, this adds the accession number to the existing MediCopia-generated specimen identification code, which provides a single entity within the MediCopia database that references both the MediCopia-generated unique identifier and the accession number generated by the LIS/PATH system. This is typically referred to by lab personnel as "merging" orders. Thereafter, the barcodes generated by pressing a "Barcodes" button 327 in FIG. 12. At block 328, the PATH-generated labels are thereafter placed over the labels that were affixed to the containers at block 294.

In an illustrative embodiment including multiple electronic platforms 124, most of the automated steps of FIG. 6 run within the electronic platforms 124. In such an embodiment, the electronic platform 124 communicates via a wired data network 128 or a wireless data network 130 with the central server 126 to create a unique order identification code. Specifically, each electronic platform 124 requests a unique order identification code from the central server 126 and the central server 126 responds with a unique order identification code. The unique identification codes may be stored within the database 142 of the central server 126 and the unique identification codes and other pertinent data may be stored within the database 138 of each individual electronic platform 124. In other illustrative embodiments, the database 142 of the central server 126 may store all relevant data. In still other illustrative embodiments, any number of the automated steps may run on the electronic platforms 124 and/or the central server 126.

While a requisition form is disclosed and/or used in the system and method for pathology specimen collection 120, the term requisition form is intended to include any request documentation or request mechanism.

While the system and method for pathology specimen collection 120 is discussed herein as being integrated with an LIS/PATH system, the system may alternatively be utilized in conjunction with any other laboratory, hospital, and/or other systems and/or as part of a subsystem of a larger system including multiple subsystems. If other systems are used with the system disclosed herein or the system is a subsystem of a larger system, one or more user interfaces may be utilized to separate the various systems/subsystems. For example, if an overall system includes both a pathology specimen collection subsystem and a biological specimen collection subsystem, each subsystem may be accessed independently of the other subsystem. In one embodiment, the overall system may include a user interface allowing a user to enter the independent subsystems.

The systems and methods for pathology specimen collection disclosed herein provide many benefits. In particular, manually written requisition forms and information included on a specimen container are often incomplete and/or unreadable. In addition, the information from the manually written requisition forms may be misread and/or mis-entered upon entering into the PATH system, thereby creating at least two places for error within the process. One benefit of the systems and methods for pathology specimen collection disclosed herein is that barcodes are created for both the specimen containers and the requisition form, which can be read by a scanner into the PATH system, thereby reducing the risk of error.

Current tracking of pathology specimens is based either on a physical number of pathology specimens or the manually written requisition forms, both of which may be inaccurate. By utilizing sequential identification codes or numbers, bundling pathology specimens together, and avoiding manual entry through the use of scanned barcodes, the potential for lost specimens is significantly reduced. Regardless of whether something is called a code or a number herein, any of such numbers or codes may include any of letters, numbers, alpha-numeric characters, or any other suitable characters.

The systems and methods for pathology specimen collection disclosed herein also provide positive patient identification. The wristband of a patient must be scanned at the bedside of a patient before printing a label for pathology specimen collection. In this manner, the patient is positively identified prior to pathology specimen collection.

Patient safety is enhanced in the systems and methods for pathology specimen collection as disclosed herein through positive patient identification, proper container tracking, and integration with other applications, such as specimen collection applications, transfusion applications, medication administration applications, and vitals measurement applications.

The systems and methods for pathology specimen collection disclosed herein may be utilized with respect to any pathology specimen collection that are collected at any inpatient or outpatient location. Without limiting the present disclosure, examples of such pathology specimen collection include a mole excised by a dermatologist, a sample from a colonoscopy obtained in an outpatient setting, a needle biopsy aspiration of a prostate, a section of an organ excised during surgery, or any specimen collected in advance of processing by a pathologist.

While the various screen shots of the embodiment of FIGS. 7-12 are shown as having a number of different fields and various information, the fields and information provided by the screens and/or provided to these screens may be varied without departing from the scope of the present disclosure. Still optionally, while various fields may be provided in the disclosed screens, any number of fields may be required or optional.

Any of the embodiments described herein may be modified to include any of the structures or methodologies disclosed in connection with other embodiments.

Numerous modifications to the present disclosure will be apparent to those skilled in the art in view of the foregoing description. Accordingly, this description is to be construed as illustrative only and is presented for the purpose of enabling those skilled in the art to make and use the embodiments of the disclosure and to teach the best mode of carrying out same. The exclusive rights to all modifications which come within the scope of the appended claims are reserved.

We claim:

1. A computer-implemented method for tracking and identifying a pathology specimen after collection, the method comprising the steps of:
creating a unique order identification code for at least one pathology specimen at a point of collection of the pathology specimen at a patient's bedside, in an operating room, or at an outpatient location and at a first location remote from where the pathology specimen is processed;
creating a pathology specimen record with a unique specimen identification code for at least one pathology specimen at the point of collection of the pathology specimen and at the first location remote from where the pathology specimen is processed;
creating a label for application to a container holding the pathology specimen at the point of collection of the pathology specimen and at a second location remote from where the pathology specimen is processed, wherein the label includes the unique specimen identification code;
forwarding the pathology specimen and the label to a laboratory remote from the first and second locations for processing;
creating an order with a unique accession number after the container is forwarded for processing at the laboratory remote from the first and second locations, by scanning the label; and
associating, at the laboratory, the unique order identification code with the unique accession number.

2. The computer-implemented method of claim 1, further including the step of creating a second label for application to a requisition form associated with the order, wherein the second label includes a unique requisition identification and wherein the step of creating an order is performed by scanning the label or the second label.

3. The computer-implemented method of claim 1, further including the step of performing positive patient identification prior to creation of an order and creation of a pathology specimen record.

4. The computer-implemented method of claim 3, wherein the step of performing positive patient identification includes the step of associating a patient record with the patient upon scanning of a wristband on the patient.

5. The computer-implemented method of claim 4, wherein the unique order identification code is associated with each of the unique specimen identification codes.

6. The computer-implemented method of claim 1, wherein the step of creating a pathology specimen record is repeated for multiple pathology specimens collected for the patient, a pathology specimen record is created for each pathology specimen, and a unique specimen identification code is created for each pathology specimen collected.

7. The computer-implemented method of claim 1, wherein the step of creating a first label includes the step of including a barcode on the first label and the step of creating an order with a unique accession number includes the step of scanning the barcode and uploading into a database the data contained in the barcode.

8. The computer-implemented method of claim 1, wherein the step of creating a second label includes the step of including a barcode on the second label and the step of creating an order with a unique accession number includes the step of scanning the barcode and uploading into a database the data contained in the barcode.

9. A computer-implemented method for tracking and processing a pathology specimen after collection, the method comprising the steps of:
creating a requisition with a unique requisition identification at a point of collection of the pathology specimen and at a location remote from where the pathology specimen is processed, wherein the requisition is based on at least one pathology specimen;
creating a pathology specimen record with a unique specimen identification code for the at least one pathology specimen at a point of collection of the pathology specimen and at the location remote from where the pathology specimen is processed, wherein the unique specimen identification code is associated with the unique requisition identification;
creating a first label including the unique requisition identification for association with a requisition form at a point of collection of the pathology specimen and at the location remote from where the pathology specimen is processed;

creating a second label including the unique specimen identification code for association with the at least one pathology specimen at a point of collection of the pathology specimen and at the location remote from where the pathology specimen is processed; and creating an order with a unique accession number after the requisition form with first label and the at least one pathology specimen with second label are forwarded for processing, by scanning the first or second label, wherein scanning the first label provides an indication to a user of all unique specimen identification codes associated with the unique requisition identification of the first label.

10. The computer-implemented method of claim 9, further including the step of performing positive patient identification prior to creation of an order and creation of a pathology specimen record.

11. The computer-implemented method of claim 10, wherein the step of performing positive patient identification includes the step of associating a patient record with the patient upon scanning of a wristband on the patient.

12. The computer-implemented method of claim 9, wherein the step of creating a pathology specimen record is repeated for multiple pathology specimens collected for the patient, a pathology specimen record is created for each pathology specimen, and a unique specimen identification is created for each pathology specimen collected.

13. The computer-implemented method of claim 12, wherein the unique order identification code is associated with each of the unique specimen identifications.

14. The computer-implemented method of claim 9, wherein the step of creating a label includes the step of including a barcode on the label and the step of creating an order with a unique accession number includes the step of scanning the barcode and uploading into a database the data contained in the barcode.

15. A computer system for tracking and identifying a pathology specimen, the computer system comprising:

at least one processor;

a network interface;

a memory element coupled to the processor, the memory storing instructions to direct the processor to perform operations comprising:

creating a unique order identification code for at least one pathology specimen at a point of collection of the pathology specimen at a patient's bedside, in an operating room, or at an outpatient location and at a first location remote from where the pathology specimen is processed;

creating a pathology specimen record with a unique specimen identification code for the at least one pathology specimen at the point of collection of the pathology specimen and at the first location remote from where the pathology specimen is processed;

creating a label for application to a container holding the pathology specimen at the point of collection of the pathology specimen and at a second location remote from where the pathology specimen is processed, wherein the first label includes the unique specimen identification code;

forwarding the pathology specimen and the label to a laboratory remote from the first and second locations for processing;

creating an order with a unique accession number after the container has been forwarded for processing at the laboratory remote from the first and second locations, by scanning the label; and associating, at the laboratory, the unique order identification code with the unique accession number.

16. The system of claim 15, wherein the memory element further stores instructions to direct the processor to perform the operation comprising: creating a second label for application to a requisition form, wherein the second label includes a unique requisition identification and wherein the step of creating an order is performed by scanning the label or the second label.

* * * * *